United States Patent
Schilling

(10) Patent No.: US 7,812,605 B2
(45) Date of Patent: Oct. 12, 2010

(54) TEST OBJECT FOR NUCLEAR SPIN TOMOGRAPHS

(75) Inventor: Harry Schilling, Eichstaett (DE)

(73) Assignee: Schleifring und Apparatebau GmbH, Fuerstenfeldbruck (DE)

( * ) Notice: Subject to any disclaimer, the term of this patent is extended or adjusted under 35 U.S.C. 154(b) by 223 days.

(21) Appl. No.: 11/538,509

(22) Filed: Oct. 4, 2006

(65) Prior Publication Data

US 2007/0262774 A1    Nov. 15, 2007

(30) Foreign Application Priority Data

Nov. 4, 2005  (EP)  .................... 05024069

(51) Int. Cl.
G01V 3/00 (2006.01)
(52) U.S. Cl. ...................................... 324/318
(58) Field of Classification Search .......... 324/300–322
See application file for complete search history.

(56) References Cited

U.S. PATENT DOCUMENTS

| | | | | |
|---|---|---|---|---|
| 4,551,678 A | * | 11/1985 | Morgan et al. | 324/300 |
| 4,646,334 A | * | 2/1987 | Zerhouni | 378/18 |
| 4,774,957 A | * | 10/1988 | Nambu et al. | 600/414 |
| 4,873,707 A | * | 10/1989 | Robertson | 378/18 |
| 4,888,555 A | * | 12/1989 | Vaughan et al. | 324/318 |
| 5,172,059 A | * | 12/1992 | den Boef | 324/307 |
| 5,227,627 A | * | 7/1993 | Gamarnik et al. | 250/252.1 |
| 5,521,955 A | * | 5/1996 | Gohno et al. | 378/18 |
| 5,590,165 A | * | 12/1996 | Gohno et al. | 378/18 |
| 6,052,611 A | * | 4/2000 | Yanof et al. | 600/429 |
| 6,315,447 B1 | * | 11/2001 | Nord et al. | 378/207 |
| 6,318,146 B1 | * | 11/2001 | Madsen et al. | 73/1.86 |
| 6,352,860 B1 | * | 3/2002 | Madsen et al. | 436/8 |
| 6,635,486 B2 | * | 10/2003 | Madsen et al. | 436/8 |
| 6,675,035 B1 | * | 1/2004 | Grable et al. | 600/411 |
| 6,720,766 B2 | | 4/2004 | Parker et al. | |
| 6,768,925 B2 | * | 7/2004 | Fenn et al. | 607/101 |
| 6,807,446 B2 | * | 10/2004 | Fenn et al. | 607/101 |
| 6,990,222 B2 | * | 1/2006 | Arnold | 382/131 |

(Continued)

FOREIGN PATENT DOCUMENTS

DE    19904635    8/1999

(Continued)

OTHER PUBLICATIONS

European Search Report, EP05024069, dated Mar. 6, 2006.

(Continued)

Primary Examiner—Brij B Shrivastav
Assistant Examiner—Dixomara Vargas
(74) Attorney, Agent, or Firm—Kevin L. Daffer; Daffer McDaniel, LLP

(57) ABSTRACT

A phantom for examination in nuclear spin tomographs comprises at least one test body for abstract imitation of a human or animal body part, and also means for supplying the test body with a liquid during the examination by nuclear spin tomography. Another phantom for examination in nuclear spin tomographs comprises at least one abstract imitation of a human or animal body part, of which at least one abstract imitation is adapted to be an at least partially flexible test body, and a flexible layer surrounding the partially flexible test body to imitate a lipid layer. Methods for producing test bodies include molding the test bodies from plastic material.

10 Claims, 1 Drawing Sheet

U.S. PATENT DOCUMENTS

| | | | |
|---|---|---|---|
| 7,122,012 B2 * | 10/2006 | Bouton et al. | 600/587 |
| 7,288,759 B2 * | 10/2007 | Frangioni et al. | 250/252.1 |
| 7,289,634 B2 * | 10/2007 | Grove | 381/67 |
| 7,336,986 B2 * | 2/2008 | Miyoshi et al. | 600/410 |
| 7,402,819 B2 * | 7/2008 | Saracen | 250/492.1 |
| 2005/0110490 A1 | 5/2005 | Zhao et al. | |
| 2005/0139758 A1 | 6/2005 | White et al. | |

FOREIGN PATENT DOCUMENTS

| | | | |
|---|---|---|---|
| FR | 2705775 | | 2/1995 |
| FR | 2708775 | | 2/1995 |
| JP | 01086952 A | * | 3/1989 |

OTHER PUBLICATIONS

Patent Abstracts of Japan, 2004-275682, Oct. 7, 2004.

Wei et al., "Deformable registration for integration of MRI/MRSI information in TRUS-guided prostate biopsy," Proceedings of SPIE, vol. 5747, Apr. 2005, pp. 1263-1273.

Mizowaki et al., "Towards Integrating Functional Imaging in the Treatment of Prostate Cancer with Radiation: the Registration of the MR Spectroscopy Imaging to Ultrasound/CT Images and its Implementation in Treatment Planning," Int. J. Radiation Oncology Biol. Phys., vol. 54, No. 5, Aug. 2002, pp. 1558-1564.

Patent Abstracts of Japan, 64-086952, Mar. 31, 1989.

Reynier et al., "MRI/TRUS data fusion for prostate brachytherapy. Preliminary results," Med. Phys. vol. 31, No. 6, Jun. 2004, pp. 1568-1575.

Firle et al., "Mutual Information based Registration for Ultrasound and CT Datasets," Proceedings of SPIE, vol. 5370, May 2004, pp. 1130-1138.

* cited by examiner

TEST OBJECT FOR NUCLEAR SPIN TOMOGRAPHS

PRIORITY CLAIM

The present application claims priority to European Patent Application No. 05024069.6 filed Nov. 4, 2005.

BACKGROUND OF THE INVENTION

1. Field of the Invention

The invention relates to test objects for nuclear spin tomography, and in particular to objects for simulating human and animal bodies. Nuclear spin tomography is also referred to as magnetic resonance tomography, MRT for short.

2. Description of the Prior Art

Various test objects are known for use in nuclear spin tomography. These test objects are frequently also referred to as phantoms.

Thus, U.S. Pat. No. 6,720,766 discloses a test object having different configurations along various spatial axes. With a test object of this kind, resolution, contrast and accuracy can be checked.

US 2005/0110490 discloses an active test object having a coil system that is capable of resonance and can be controlled to interact with the field of the nuclear spin tomograph.

US 2005/0139758 discloses an imitation of joints of a human body.

Phantoms known from prior art are substantially abstract test objects for achieving mainly the object of calibrating nuclear spin tomographs. With test objects of this kind, examinations are not possible under the extremely complex conditions present in human bodies. In accordance with prior art, they must be performed on test persons, as before.

BRIEF SUMMARY OF THE INVENTION

It is the object of the invention to introduce a phantom for simulating conditions prevailing in a human or animal body with sufficient accuracy, so that realistic measurements can be performed and surgical operating techniques and examination techniques can be tested. In particular, a device in accordance with the invention is intended to provide as realistically as possible an imitation of a human prostrate gland and its surroundings which will provide reproducible results and also can be manufactured at low cost. Another object is to provide a method for examination by nuclear spin tomography on a test body which is an abstract imitation of at least one human or animal body part, Further objects are to provide a method for manufacturing the test body, and to provide a method for manufacturing an imitation of a lipid layer on a test body.

In accordance with the present invention the first object is achieved by a phantom for examination in nuclear spin tomographs, comprising: at least one abstract imitation of a human or animal body part, of which at least one abstract imitation is adapted to be a test body; and means for supplying at least one part of the phantom with a liquid during examination by nuclear spin tomography. The object is also achieved by a phantom for examination in nuclear spin tomographs, comprising: at least one abstract imitation of a human or animal body part, of which at least one abstract imitation is adapted to be an at least partially flexible test body; and a flexible layer surrounding the partially flexible test body to imitate a lipid layer.

For achievement of the other objects, the present invention provides a method for examination by nuclear spin tomography on an abstract imitation of at least one human or animal body part, the method comprising the step of causing a liquid to flow through at least one part of the imitation during the examination; and a method for manufacturing a test body which is an abstract imitation of a human or animal body part for examination by nuclear spin tomography, the method comprising the steps of immersing a mold for the test body in a liquid plastic material and subsequently curing the plastic material; and also a method for manufacturing an imitation of a lipid layer on a test body representing an imitation of a human or animal body part for examination by nuclear spin tomography, the method comprising the steps of immersing a test body in a liquid plastic material and subsequently hardening or curing the plastic material adhering to the test body.

BRIEF DESCRIPTION OF THE DRAWING

In the following the invention will be described by way of example, without limitation of the general inventive concept, on examples of embodiment with reference to the drawings.

DETAILED DESCRIPTION OF PREFERRED EMBODIMENTS

Figure 1:
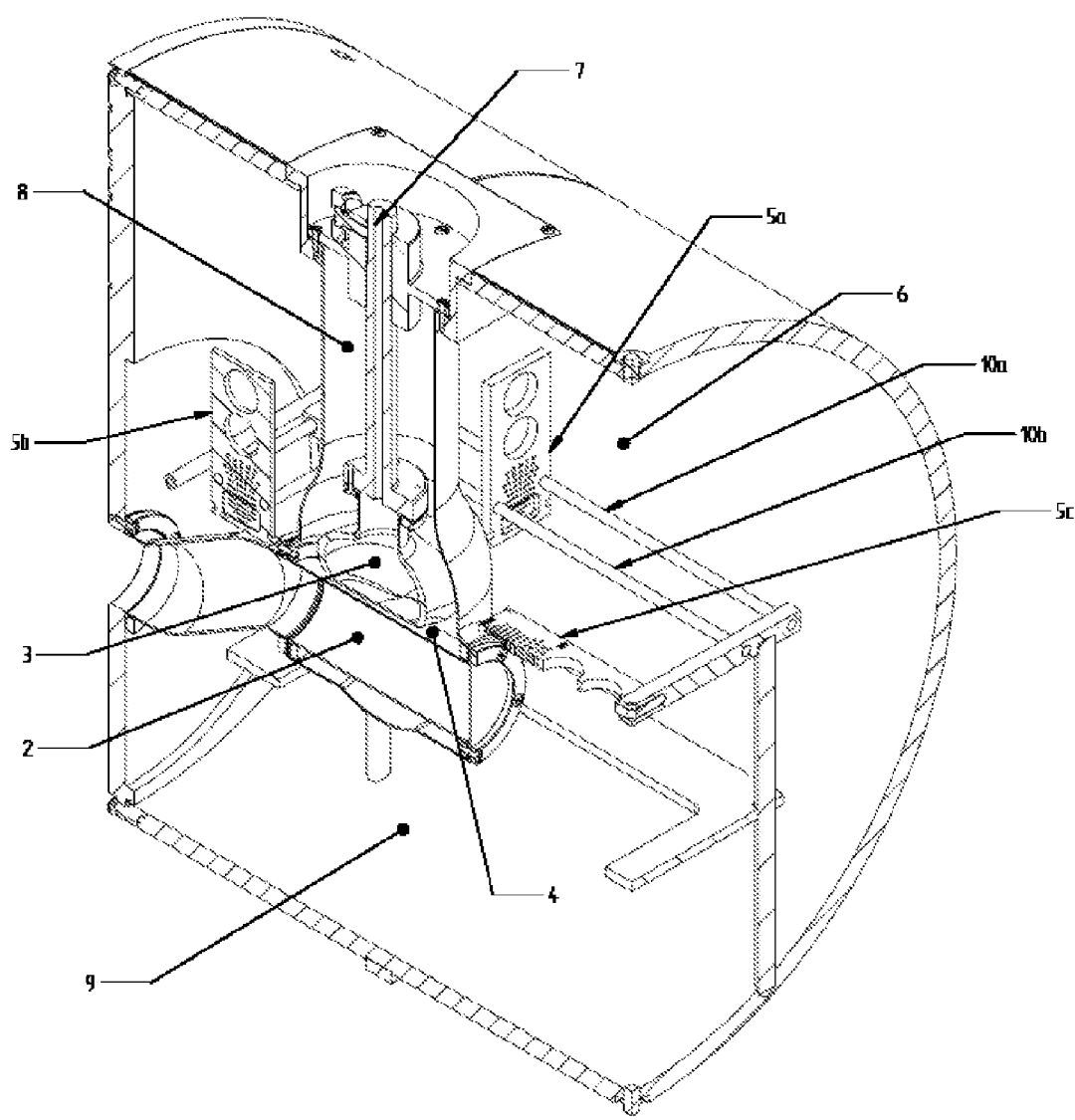
FIG. 1 shows an example of an arrangement in accordance with the invention.

FIG. 1 shows an example of a prostrate-gland phantom in accordance with the invention. A test body 3 in the form of a prostrate-gland imitation, and also another test body 2 in the form of an imitation of a rectum are located within a vessel 6. An imitation of a lipid layer 4 is disposed around the imitation of the prostrate gland 3. The prostrate-gland imitation 3 is connected to the vessel 6 by means of a holder 7, here for example in the form of a tube. The position of this holder can be adjusted so that the shape and location of the prostrate-gland imitation 3 can be adjusted from the outside. In this example, a hollow space is dimensioned so that the prostrate-gland test body 3 may be removed and modified or exchanged through the hollow space. A liquid for simulating the lipid layer can be introduced into the hollow space 8. A check of the resolution and a calibration of the nuclear spin tomograph along three axes is possible by means of resolution patterns 5a, 5b, 5c. The inside volume 9 of the phantom is filled with a liquid, for example an aqueous salt solution, for loading the resonance coils of the nuclear spin tomograph. Conduits 10a, 10b serve to simulate blood vessels and flow artifacts caused by blood flow. Preferably a not shown pump is provided for supply. Alternatively, the conduits may also be supplied from infusion flasks or other vessels. The conduits are here designed to be straight tubes and therefore to have exactly defined positions. They may simultaneously also serve other functions, such as supporting resolution patterns. Alternatively, the conduits are disposed in the form of blood vessels as present in a human body.

A phantom 1 in accordance with the invention, as intended for examinations in nuclear spin tomographs, comprises at least one test body 2, 3 for abstractly imitating at least one part of a human or animal body. Furthermore, at least one means is provided for supplying a liquid to, or passing a liquid through, at least one portion of the test body during an examination by nuclear spin tomography. The liquid may be a body fluid, for example blood, urine, or a suitable imitation. The portion of the test body through which the liquid flows may be configured to simulate the corresponding fluid-carrying vessels of a human or animal body, for example blood vessels such as arteries or veins. The supply of liquid may be effected from a storage vessel such as an infusion flask, for example.

It is of more advantage to pass the liquid through a closed circuit, for example, by means of a pump. With this, the consumption of liquid is smaller. Therefore, a test body in accordance with the invention preferably has means for connecting hoses or tubes, or itself comprises hoses or tubes.

With this kind of embodiment of the invention, effects (flow artifacts) of a moving liquid on an examination performed by nuclear spin tomography may be investigated in a reproducible manner.

A method, in accordance with the invention, for performing an examination by nuclear spin tomography on an abstract imitation of at least one human or animal body part is characterized by at least one part of the imitation being flushed with a liquid during the examination.

Another phantom 1 for performing an examination in nuclear spin tomographs comprises at least one test body 2, 3 for abstractly imitating at least one human or animal body part. The test body is designed to be at least partly elastically deformable, and to be surrounded by another flexible layer. This layer is intended to simulate a typical lipid layer.

A fine tuning of resonances, and also quantitative assessments of new coils and systems, are possible with the phantoms of the present invention. Investigation and optimization of new sequences, and also clinical quality assurance can be improved and performed at lower cost.

The resonance behavior of coils used in nuclear spin tomographs is very strongly dependent on the geometry of the bodies to be examined, and also on their electrical characteristics. For the design and fine tuning of the coils it is therefore necessary to simulate as true to nature as possible, and also reproducibly, the electrical conditions (resistive, capacitive and inductive) that may arise.

Basically a phantom makes it possible to obtain reproducible measurement results. It represents an objective reference standard for new methods and processes, and also for an implementation of new hardware. With the aid of a phantom, a direct comparison of changed parameters and sequences, various systems, and coils and field strengths is possible.

A phantom having a defined composition and known geometric shape is also indispensable for quality assurance. For clinical studies the technical systems should be calibrated regularly in order to safeguard comparable measurement results. This is possible only with standardized models.

The outer dimensions of the phantoms 1 in accordance with the invention, and also the dimensions of the test bodies 2, 3, preferably correspond to the actual dimensions of average human beings. The entire body mass is based preferably on appropriate standards.

In a particularly advantageous embodiment of the invention, at least one test body comprises an imitation of a male prostrate gland.

Another advantageous embodiment of the invention provides at least one additional imitation 2 of at least one other body part such as a rectum or a pelvis. An incorporation of additional body parts makes it possible to achieve an even more realistic imitation.

In another advantageous embodiment of the invention, at least one imitation of another body part or a test body is mechanically linked with other parts, or even test bodies, by means of tissue imitations, so that the mechanical coupling corresponds to that of a natural body. Thereby certain movements of a patient, and also those occurring during an insertion of instruments, for example rectal probes, may be simulated.

In another advantageous embodiment, parts and particularly test bodies, such as an imitation 3 of a prostate gland within a complex phantom simulating, for example, a complete pelvis region, are exchangeable. With this, any changes of single parts in an environment that otherwise is reproducibly constant can be examined. For example, the different characteristics of a prostrate gland that is enlarged when compared with small, tumor-affected when compared with healthy, or adipose when compared with low in fat, may be studied and tested.

Another embodiment of the invention comprises at least one test body 3 of a shape corresponding to that of an organ of a human body. Preferably a test body of this kind has the shape of a male prostrate gland. Furthermore, this test body is disposed preferably in a realistic relationship to other body parts. Thus, a test body having the shape of a prostrate gland should cover up to 30% of an imitation of a rectum, and be spaced from this by 1 mm to 2 mm. The resulting gap between the imitation of the prostrate gland and the imitation of the rectum is preferably filled with a lipid layer 4. For these imitations it is of importance that both the imitation 2 of the rectum, and also the imitation 3 of the prostrate gland be flexible, but of stable shape. This arrangement results in a flexible connection of the two parts without any rigid coupling, in correspondence with an actual human body. Flexible plastic materials such as thin PVC, for example, may be used for this.

In alternative test bodies a particular organ could be substituted by, for example, a cube, a cylinder, or other geometrical bodies. Although this is not a very realistic imitation with which real applications can be investigated, nevertheless calibrations may be more easily performed with simple geometric shapes, because the positions of corners and edges, and also other geometrical features, are exactly known. Furthermore, geometrical bodies are usually more easy to manufacture.

A particularly expedient embodiment of the invention comprises at least one test body 3 having a variable position within the phantom. With this, the position can be adjusted advantageously from the outside. Thus, for example, a test body 3 having the shape of a prostrate gland can be provided on a tube 7, the position of which relative to the phantom can be varied by means of an outer screw-thread. Thereby, the thickness of the lipid layer may also be set indirectly.

A method in accordance with the invention for producing test bodies, preferably in the shape of a prostrate gland, comprises the steps of immersing a mold in a liquid plastic material, following by curing the plastic material. The mold for manufacturing a test body may be produced, for example, by stereo-lithography (rapid-prototyping), or also by an LOM method or CNC milling. Preferably the test body can be subsequently filled with a filing material, for example gelatin with additives, to simulate tissue. For this, the test body is stored preferably in a vessel with a material such as water or glass beads to produce a counter-pressure. Thereby deformations during filling can be avoided.

A sheath of fatty tissue (lipid layer) of an organ or a body part, in particular a prostrate gland, may be reproduced accordingly. For this, the test body for the organ or the prostrate gland is immersed in a suitable liquid that subsequently solidifies or hardens.

A phantom 1 in accordance with the invention is preferably fabricated to be of at least two parts. In this, the upper part of the phantom forms mainly the electromagnetic load on the coils. The lower part of the phantom comprising rectum and prostrate gland contains all substantial components for spectroscopic and image-forming quality measurement. Advantageously, all components are designed so that they are stable in vacuum and can be degassed easily. In addition, the components are configured so that they can be easily filled and can be exchanged just as easily within the phantom. As it cannot be ensured that all gas will be removed, despite a degassing operation, each component of the phantom is designed so that any remaining gas can collect in locations of the components which are not relevant to image formation. These locations are removed as far as possible from the centers of the test bodies. The components are advantageously fabricated to have thin walls in order to avoid discontinuities of susceptibility.

Furthermore, it is of advantage for a resolution pattern 5a, 5b, 5c, having a defined geometry to be provided additionally. With this, an exact calibration of the spatial components and the corresponding resolution can then be effected.

Furthermore, it is of advantage for visible markings for position checks to be provided on at least one test body (2, 3).

The invention claimed is:

1. A phantom, comprising:
   at least one abstract imitation of a whole, and thereby more than a slice, of a human or animal body part for calibrating nuclear spin tomographs, wherein the at least one abstract imitation is an elastically deformable test body, and wherein a position of the test body inside the phantom is changed and adjusted by movement of a holder from outside the phantom without removing the test body from the phantom; and
   a flexible layer surrounding the elastically deformable test body to imitate a lipid layer.

2. The phantom according to claim 1, wherein at least one abstract imitation of a human or animal body part is mechanically linked to another abstract imitation of a human or animal body part by a tissue imitation forming a mechanical coupling corresponding to that in a natural body.

3. The phantom according to claim 1, wherein at least one abstract imitation of a body part is adapted to be exchanged for another abstract imitation of a body part.

4. The phantom according to claim 1, further comprising at least one resolution pattern.

5. The phantom according to claim 1, further comprising visible markings on at least one test body for position control.

6. The phantom according to claim 1, wherein at least one test body is shaped as a human or animal organ.

7. The phantom according to claim 1, wherein at least one test body comprises an imitation of a male prostrate gland.

8. The phantom according to claim 7, further comprising at least one imitation of another body part.

9. The phantom according to claim 8, wherein the another body part is a rectum or a pelvis.

10. The phantom according to claim 1, wherein the phantom is a complex phantom reproducing a complete pelvic region, and a test body that is an imitation of a prostrate gland in the complex phantom is exchangeable for another test body that is an imitation of a prostrate gland.

* * * * *